United States Patent [19]

Lawrence et al.

[11] Patent Number: 4,791,820

[45] Date of Patent: Dec. 20, 1988

[54] APPARATUS MODULE FOR COLLECTION OF VOLATILES FROM TEST SAMPLE

[75] Inventors: Lowell J. Lawrence; Scott R. Hamann; Abbe L. Kesterson, all of Lexington, Ky.; Luis O. Ruzo, Berkley, Calif.

[73] Assignee: Pharmacology & Toxicology Research Laboratory, Lexington, Ky.

[21] Appl. No.: 80,621

[22] Filed: Jul. 31, 1987

[51] Int. Cl.[4] .............................................. G01N 1/26
[52] U.S. Cl. .............................. 73/863.21; 73/864.34; 73/864.81; 422/80
[58] Field of Search ............ 73/863.31, 863.32, 864.51, 73/863.85, 864.81, 864.82, 864.83, 864.84, 864.85, 863, 864.91, 863.21, 864.34; 422/68, 80, 91, 83, 102

[56] References Cited

U.S. PATENT DOCUMENTS

| | | | |
|---|---|---|---|
| 3,879,503 | 4/1975 | Peterson | 261/89 X |
| 3,925,022 | 12/1975 | Showalter et al. | 73/23.1 X |
| 4,008,393 | 2/1977 | Rapkin | 250/238 X |
| 4,208,285 | 6/1980 | Sample, Jr. | 210/180 |
| 4,209,299 | 6/1980 | Carlson | 422/98 X |
| 4,395,903 | 8/1982 | Gouw | 73/64.2 |
| 4,453,424 | 6/1984 | Hacket | 73/864.58 |
| 4,671,298 | 6/1987 | Babb et al. | 422/109 X |

OTHER PUBLICATIONS

Aikens et al., *Integrated Experimental Chemistry*, vol. 1, 1978, pp. 72 and 73.

*Primary Examiner*—Tom Noland
*Attorney, Agent, or Firm*—King and Schickli

[57] ABSTRACT

An apparatus module for volatile collection, such as may be utilized in solution photolysis of a test sample, includes a vessel member that is sealingly connected to a vapor collection adapter. The vapor collection adapter includes an inlet for the delivery of gas into the vessel and an outlet for directing gas and volatiles emitted by the test sample from the vessel. The vessel member is elongated and mounted in a generally upright position by means of a peg that extends from a closed end of the vessel. This peg is received within an aperture in an underlying support rail. The apparatus is also specially adapted for mounting in series. More specifically, the support rail includes a series of equally spaced apertures for holding a number of modules at evenly spaced intervals. In addition, cooperating ball and socket connectors are provided at the distal ends of the inlet and outlet so as to allow sealed connection of adjacent modules together.

10 Claims, 2 Drawing Sheets

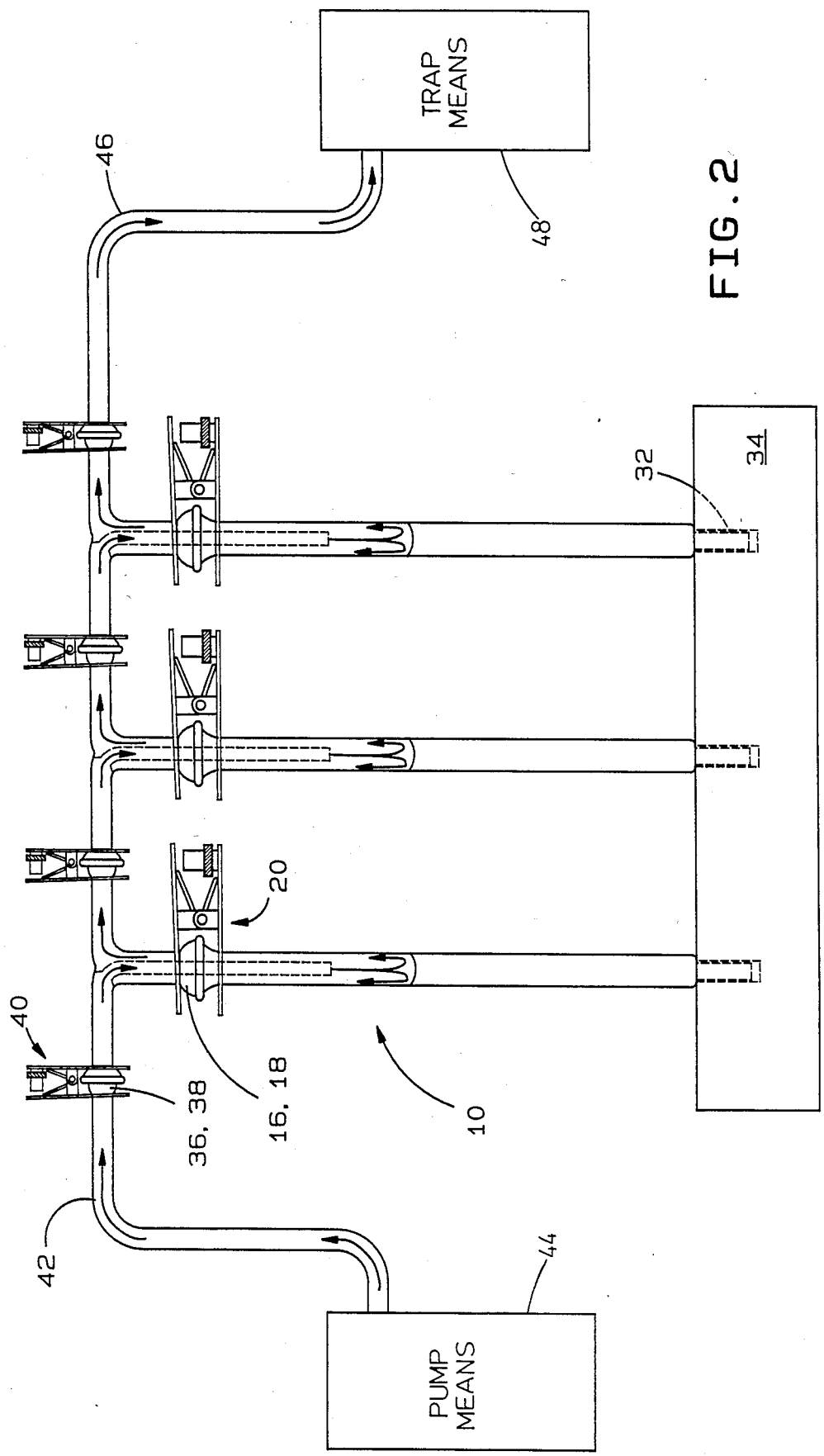

APPARATUS MODULE FOR COLLECTION OF VOLATILES FROM TEST SAMPLE

TECHNICAL FIELD

The present invention relates generally to the chemical apparatus field and, more particularly, to a test apparatus specially designed for use in collecting volatiles from a test sample undergoing solution photolysis.

BACKGROUND OF THE INVENTION

Over the years the agricultural and forestry industries have turned increasingly to science to help feed and house the ever increasing human population. Through the development of various herbicides, fertilizers, insecticides and pesticides for terrestial crop and forestry uses, man has been able to markedly improve the productivity of the land. The increases in crop and timber production, however, have not been obtained without suffering some adverse consequences.

More particularly, many of the herbicides, fertilizers, insecticides and pesticides that have been developed detrimentally impact the environment in one way or another when used in certain concentrations or under certain conditions. Livestock poisonings, fish kills, and other cataclysmic events have resulted. For example, many insecticides such as DDT are particularly stable and resistant to destruction by light and oxidation. With continued use, concentrations of such insecticides may build up in the environment over time to dangerous levels. This may lead to widespread death of wildlife and contamination of water supplies deleteriously affecting downstream population centers.

The problem has not gone unnoticed by the government. The Environmental Protection Agency has recently devised new tests specifically designed to collect the data necessary for evaluating the hazard inherent in these types of chemicals. One of the studies developed by the government for evaluating the overall environmental impact of, for example, a pesticide, is a full degradation study in water.

When pesticides are introduced into aqueous systems in the environment either directly or by leaching of runoff after terrestrial application, they may undergo photolytic transformation by sunlight. Photolysis is the interaction of a compound with light. More specifically, light energy is transferred to the chemical bonds of the compound, either directly or indirectly through another compound. This energy serves to break the bonds and the original compound is transformed to other compounds known as photoproducts. The purpose of the photodegradation or solution photolysis studies is to obtain data on rates of photolysis and half-lives of the parent pesticide and its photodegradates to establish the importance of this transformation process and the persistence characteristics of photoproducts that may be formed.

Exacting test procedures have been developed to accurately determine the rates of agueous photolysis of pesticides ($t_{\frac{1}{2}}$) and to identify photolytic products and rates of formation and decline of these products. The procedures are standardized so that results of various studies, even when conducted by different groups, may be effectively compared.

Preferably, the test samples are exposed to natural sunlight conditions. Thus, the vessels for containing the test samples must be supported in a way so as not to block the passage of light to the samples. In addition, the vessels themselves must be optically pure so as not to filter out any of the radiation of natural sunlight.

A further concern relates to the need to minimize the loss of the test sample through volatilization. In order to accurately determine the photolysis rate of the test sample, the volatiles emitted by the test sample should be collected. Further, these volatile photoproducts should be identified if emitted in any appreciable level. Thus, in order to carry this procedure out, the test sample vessel must be sealed and provide some means for collecting the emitted volatiles. In addition, the test sample solution needs to be available for periodic testing at specific time intervals in order to allow determination of the photoproducts produced within the solution by photolysis.

Past apparatus that have been developed for this purpose have been cumbersome and difficult to use effectively. Such apparatus have actually promoted mistakes during testing that prevent them from providing accurate analytical data in accodance with the rigid test requirements set by the Environmental Protection Agency. A need is therefore identified for an apparatus specially designed for use in performing solution photolysis studies that is simple to use effectively.

SUMMARY OF THE INVENTION

Accordingly, it is a primary object of the present invention to provide a solution test apparatus that may be securely mounted in position without interfering with the free passage of light to a test sample contained within the apparatus.

Another object of the present invention is to provide an apparatus for testing a solution that may be conveniently utilized for collection of volatiles from a test sample undergoing degradation studies.

Yet another object of the present invention is to provide an apparatus for containing a test sample of a solution in a sealed environment that is also specially adapted for connection in series with another such apparatus. In this way the apparatus allows not only the collection and identification of volatiles emitted by the test sample over time, but also actual testing of the test sample at various time intervals without disturbing the entire apparatus and significantly disrupting the test.

Additional objects, advantages, and other novel features of the invention will be set forth in part in the description that follows and in part will become apparent to those skilled in the art upon examination of the following or may be learned with the practice of the invention. The objects and advantages of the invention may be realized and attained by means of the instrumentalities and combinations particularly pointed out in the appended claims.

To achieve the foregoing and other objects, and in accordance with the purposes of the present invention as described herein, an improved apparatus is provided for the collection of volatiles from a test solution. More specifically, the apparatus is especially adapted for the collection of volatiles produced during solution photolysis studies of a test sample, such as presently required under Environmental Protection Agency regulations.

The apparatus of the present invention includes a vessel, preferably, in the form of a tube for holding a test sample. A vapor collection adapter is provided to sealingly engage and close the vessel. The vapor collection adapter is modular and includes means for sealingly connecting the apparatus of the present invention in series with another like apparatus in a building block fashion. In addition, the apparatus includes a means for mounting the vessel so as to substantially avoid any blockage of the passage of light to the test sample in the vessel. Advantageously, the apparatus allows volatiles produced by a test sample of solution over time to be collected and analyzed. In addition, periodically a test sample in one of the serially connected apparatus modules may be analyzed without significantly disturbing the remaining modules that are connected in series. In this way, more accurate and reliable test results are provided since a number of causes for potential errors are eliminated. This includes the loss of volatiles when drawing some of the test sample solution for analysis.

More specifically, the vessel is elongated and includes a peripheral sidewall and a closed end wall. The vessel is mounted upright by means of a peg that extends from the end wall. Thus, when mounted, the extended side wall of the vessel remains unobstructed so as to allow the uninterrupted passage of light to the test sample. Further, the vessel is preferably made from an optically pure material such as quartz, so that there is no filtration of any of the radiation from the light impinging on the test sample.

A fixed support rail is provided for the mounting of the vessel. The support rail includes an aperture especially adapted to receive the peg at the bottom of the vessel. Where a number of the vessels are to be connected as a modular group in series, the rail includes equally spaced apertures each designed to receive a mounting peg of a vessel. When mounted in this manner, the vessels are provided at evenly spaced intervals for simple connection in series through the associated vapor collection adapters.

The vapor collection adapter includes an inlet for directing gas, preferably air, into the vessel and downwardly onto the surface of the test sample. In addition, the vapor collection adapter includes an outlet for directing air and volatiles emitted by the test sample from the vessel.

More specifically, the inlet includes a delivery tube passageway substantially concentrically disposed within the outlet. The delivery tube extends downwardly into the vessel and has an opening at its end adjacent to the surface of the test sample. Thus, the gas passing through the tube is closely directed toward the surface of the sample so as to sweep volatiles from the surface. These volatiles are then swept upwardly through the vessel to and through the outlet by the gas stream. Where a number of modules are connected in series, the volatiles from each vessel are carried by the gas through the entire apparatus line and collected in a trap at the end for analysis.

The means for sealingly connecting the apparatus modules in series includes cooperating ball and socket connectors. These connectors are mounted to the distal ends of the inlet and outlet of the vapor collection adapter. Thus, for example, the ball connector at the distal end of one outlet may be sealingly connected and received within the socket connector at the distal end of an adjacent inlet. In addition, the vapor collection adapter and the top of the vessel include cooperating ball and socket connectors for sealing engagement and connection. This type of connection provides sufficient flexing or play to enable easy connection of the modules in series. Clamps, such as are known in the art, may be utilized to securely engage the connectors and provide full sealing at each connection. Thus, volatiles emitted by the test sample are positively maintained within the "closed" apparatus system for collection and analysis.

Still other objects of the present invention will become readily apparent to those skilled in this art from the following description wherein there is shown and described a preferred embodiment of this invention, simply by way of illustration of one of the modes best suited to carry out the invention. As it will be realized, the invention is capable of other different embodiments, and its several details are capable of modifications in various, obvious aspects all without departing from the invention. Accordingly, the drawing and descriptions will be regarded as illustrative in nature and not as restrictive.

BRIEF DESCRIPTION OF THE DRAWING

The accompanying drawing incorporated in and forming a part of the specification, illustrates several aspects of the present invention, and together with the description serves to explain the principles of the invention. In the drawing:

FIG. 2 is a schematical representation showing a number of the modules of the present invention mounted upright and in series for the collection of volatiles emitted by a specimen during testing.

Reference will now be made in detail to the present preferred embodiment of the invention, an example of which is illustrated in the accompanying drawing.

DETAILED DESCRIPTION OF THE INVENTION

Figure 1:
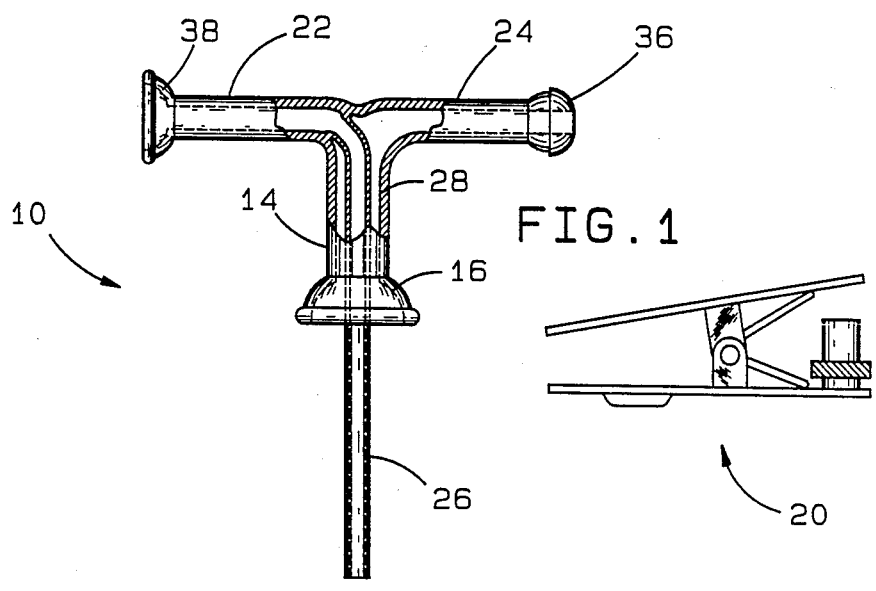
FIG. 1 is an exploded, partly cross-sectional view of the vessel, vapor collection adapter and spring clamp of the apparatus module of the present invention.
Figure 1:
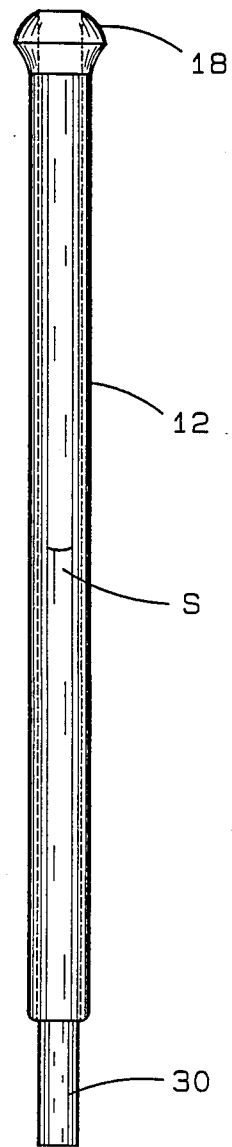

Reference is now made to FIGS. 1 and 2 showing the apparatus module 10 of the present invention for utilization in the collection of volatiles emitted from a test sample S. The invention is being described with respect to the collection of volatiles from a test sample undergoing solution photolysis. It should be recognized, however, that the module 10 in its broader aspects of the invention is not limited to such a specific application, but is being shown in this manner for purposes of illustration.

As shown in FIG. 1, each module 10 includes a vessel in the form of an elongated tube 12. Where the tube 12 is to be utilized in photolysis studies, preferably, it is mounted generally upright, as shown. The tube 12 is constructed of an optically pure material such as quartz, which does not tend to absorb and transmit different wavelengths to any appreciable extent.

A test sample S is placed within the tube 12 and the top of the tube is then sealed by means of a vapor collection adapter 14. As shown, the vapor collection adapter 14 includes a socket connector 16 specially adapted to engage a corresponding ball connector 18 forming the periphery of the top edge of the tube 12. A spring clamp 20 is then positioned over the joint so as to engage the socket and ball connectors 16, 18 and bias them together into tight sealing engagement (see also FIG. 2).

The vapor collection adapter 14 includes an inlet 22 designed specifically to direct a gas stream, such as air, down onto the surface of the test sample S. Any volatiles emitted by the test sample S are then carried by this gas stream upwardly through the tube 12 and out through the outlet 24. In order to achieve this end, the inlet 22 includes a delivery tube 26 concentrically disposed within the throat 28. Preferably, the tube 26 that extends down into the tube 12 to just above the surface of the test sample S.

The tube 12 and its corresponding vapor collection adapter 14 are specially adapted for secure mounting without interfering with the free passage of light through the sidewall of the tube to the test sample S. To achieve this end, a mounting peg 30 (see FIG. 1) is attached to and extends from the closed end wall of the tube 12 in alignment with the longitudinal axis of the tube. The peg 30 is tapered slightly so as to be readily received within a corresponding aperture 32 in a support rail 34 (see FIG. 2).

In conducting certain studies of test samples such as solution photolysis studies for the Environmental Protection Agency, it may be desirable for a number of the modules 10 of the present invention to be connected in series or building block fashion. The manner in which this is done is best shown in FIG. 2. As should be appreciated also from viewing FIG. 1, each vapor collection adapter 14 includes cooperating ball and socket connectors 36, 38 specially adapted for this purpose. More specifically, a ball 36 is mounted to the distal end of each outlet 24. A cooperating socket 38 is mounted to the distal end of each inlet 22. The support rail 34 is provided with a series of evenly spaced apertures 32. Each of the apertures is provided at the necessary interval so that the ball and socket connectors 36, 38 of adjacent modules 10 in the series meet for engagement. A spring clamp 40, similar to that described above, may be utilized to bias the connectors 36, 38 together and provide the necessary sealing to prevent the loss of volatiles from the test apparatus.

As should be appreciated, the modules 10 of the present invention are relatively simple to utilize in this type of testng and, therefore, substantially reduce the possibility of errors that can distort test results. As shown in FIG. 2, the first or lead module 10 in the series may be connected by means of a line 42 to an air (or other gas) pump, schematically shown at 44. Gas from the pump 44 passes through the tube 42 down through the inlet 22 including the delivery tube 26 to the surface of the test sample in the lead module 10. The gas carries the volatiles emitted by the test sample S in the first module 10 upwardly through the tube 12, the neck 28 and outlet 24 into the inlet 22 of the next in-line module.

The gas and volatiles collected from the first apparatus are then directed by the delivery tube 26 to the surface of the test sample S in the second module 10. Volatiles from the first and second test samples are then lifted by the gas flow up the second tube 12 through the neck 28 and outlet 24 to the inlet 22 of the next modules. There the process is again repeated as described above. Once the final module 10 in the series is reached, the gas and all the collected volatiles are delivered by means of the tube 46 to a collection trap schematically shown at 48. There, the gas and volatiles are bubbled through, for example, sulphuric acid, sodium hydroxide solution and/or ethylene glycol depending on the types of volatiles that may be expected to be produced. The trap 48 collects the volatiles for quantitative and/or qualitative analysis as desired, with the gas medium either being recycled by the pump 44 or exhausted to the atmosphere.

During certain procedures such as degradation studies, it may also become necessary to actually analyze a test sample. This may be done conveniently and efficiently with the apparatus of the present invention. Initially the pump 44 is deactivated to stop all gas flow. Then, a module 10 at either end of the series, such as the lead module, is disconnected from the line 42 and the adjacent apparatus 10. The clamps 40 are removed, the ball and socket connectors 36, 38 disconnected and the module 10 removed from the series. The tube 42 is then reconnected to the inlet 22 of the next module 10 in the series and the pump 44 restarted. In this way, the remaining test samples in the series remain undisturbed and the loss of volatiles is absolutely minimized or substantially eliminated. Further, where measured quantities of test samples are originally added to each module, the investigator has immediate knowledge of the quantity of starting material that must be accounted for in original compound and photoproducts during his analysis. Advantageously, this simple procedure eliminates a number of potential errors that could be made during testing that could significantly affect test results.

In summary, numerous benefits have been described which result from employing the concepts of the present invention. Advantageously, the present invention relates to a module that may be securely mounted in an upright position without interfering in any way with the free passage of light to the test samples through the side wall of the tube 12. Thus, the apparatus of the present invention is particularly adapted for use in photolysis studies. The module also includes a vapor collection adapter 14 having ball and socket connectors 36, 38 to allow connection of a number of the modules in series. Advantageously, the ball and socket connectors between the tube 12 and its adapter 14, as well as between adapters of adjacent tubes in series, provide the necessary play to assure tight sealing engagement that prevents the loss of volatiles.

The foregoing description of the preferred embodiment of the invention has been presented for purposes of illustration and description. It is not intended to be exhaustive or to limit the invention to the precise form disclosed. Obvious modifications or variations are possible in light of the above teachings. For example, while the modules 10 are shown in their full upright position, they may be mounted at an angle, if desired. In this instance, a lower profile of the series of modules is obtained, and a larger surface area of the test sample is provided. The preferred embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

We claim:

1. An apparatus module for collection of volatiles from a test sample, comprising:
   transparent vessel means for holding a test sample;
   vapor collection adapter means for sealingly engaging and closing said vessel means;
   means for sealingly connecting said module in series with another module holding a test sample; and
   means for mounting said vessel means so as to substantially avoid any obstruction to the passage of light to said test sample in said vessel means;
   whereby volatiles produced over time by the test samples in said module and said another module may be collected and analyzed, and the test sample in said module may be periodically analyzed substantially without disturbing the test sample in said another module in said series.

2. The apparatus set forth in claim 1, wherein said vessel means includes an elongated side wall and an end wall, said mounting means being connected only to said end wall.

3. The apparatus set forth in claim 2, wherein said mounting means includes a peg means extending from said end wall.

4. The apparatus set forth in claim 3, wherein said mounting means further includes a rail having an aperture adapted to receive said peg means.

5. The apparatus set forth in claim 4, wherein said rail includes a series of equally spaced apertures for mounting a number of said module at even intervals for connection in series.

6. The apparatus set forth in claim 1, wherein said vapor collection adapter means includes an inlet for directing gas into said vessel means and across the surface of the test sample and an outlet for directing gas and volatiles emitted by said test sample from said vessel means.

7. The apparatus set forth in claim 6, wherein said inlet includes a tube substantially concentrically disposed within said outlet that extends into said vessel means adjacent to a surface of said test sample.

8. The apparatus set forth in claim 6, wherein said connecting means includes cooperating ball and socket connections mounted to distal ends of said inlet and outlet.

9. The apparatus set forth in claim 1, wherein said vessel means and said vapor collection adapter means include cooperating ball and socket connectors for sealing engagement and connection.

10. An apparatus for the collection of volatiles produced during solution photolysis of a test sample, comprising:

multiple transparent vessel means for holding the test sample;

vapor collection adapter means connected to each vessel means for sealingly engaging and closing said vessel means;

means for sealingly connecting said vapor collection adapter means together in series;

means for mounting said vessel means so as substantially avoid any obstruction to the passage of light to said test sample in said multiple vessel means;

means for pumping gas serially through said multiple vessel means so as to carry volatiles emitted by said test sample; and trap means for collecting volatiles carried by said gas being pumped serially through said multiple vessel means whereby volatiles produced by the test sample in said multiple vessel means may be collected for analysis and the test sample in one of said vessel means may be analyzed without substantially disturbing another test sample in another of said multiple vessel means.

* * * * *